US011918394B2

(12) United States Patent
Cao et al.

(10) Patent No.: US 11,918,394 B2
(45) Date of Patent: Mar. 5, 2024

(54) RADIATION DETECTOR

(71) Applicant: SHENZHEN XPECTVISION TECHNOLOGY CO., LTD., Shenzhen (CN)

(72) Inventors: Peiyan Cao, Shenzhen (CN); Yurun Liu, Shenzhen (CN)

(73) Assignee: SHENZHEN XPECTVISION TECHNOLOGY CO., LTD., Shenzhen (CN)

(*) Notice: Subject to any disclaimer, the term of this patent is extended or adjusted under 35 U.S.C. 154(b) by 589 days.

(21) Appl. No.: 17/129,006

(22) Filed: Dec. 21, 2020

(65) Prior Publication Data

US 2021/0106296 A1 Apr. 15, 2021

Related U.S. Application Data

(63) Continuation of application No. PCT/CN2018/095524, filed on Jul. 12, 2018.

(51) Int. Cl.
*A61B 6/14* (2006.01)
*A61B 6/03* (2006.01)
*G01N 23/046* (2018.01)
*G01N 23/10* (2018.01)
*G01N 23/203* (2006.01)
*G01T 1/24* (2006.01)
*H01J 37/26* (2006.01)

(52) U.S. Cl.
CPC ............ *A61B 6/4291* (2013.01); *A61B 6/035* (2013.01); *A61B 6/14* (2013.01); *A61B 6/4233* (2013.01); *A61B 6/4275* (2013.01); *G01N 23/046* (2013.01); *G01N 23/10* (2013.01); *G01N 23/203* (2013.01); *G01T 1/241* (2013.01); *H01J 37/26* (2013.01); *G01N 2223/501* (2013.01)

(58) Field of Classification Search
CPC ......... A61B 6/4291; A61B 6/035; A61B 6/14; A61B 6/4233; A61B 6/4275; G01N 23/046; G01N 23/10; G01N 23/203; G01N 2223/501; G01T 1/241; G01T 1/17; G01T 1/247; H01J 37/26
USPC ................................ 250/306, 307, 310, 311
See application file for complete search history.

(56) References Cited

U.S. PATENT DOCUMENTS

| 4,255,659 A * | 3/1981 | Kaufman | ............... G01T 1/2928 378/19 |
| 6,420,710 B1 * | 7/2002 | Verger | .................... G01T 1/247 250/370.06 |
| 2010/0225837 A1 | 9/2010 | Seki et al. | |
| 2018/0017686 A1 * | 1/2018 | Cao | ........................ G01T 1/247 |

FOREIGN PATENT DOCUMENTS

| CN | 1892250 A | 1/2007 |
| CN | 103576179 A | 2/2014 |
| CN | 107533145 A | 1/2018 |

(Continued)

*Primary Examiner* — Michael Maskell
(74) *Attorney, Agent, or Firm* — IPRO, PLLC; Qian Gu

(57) ABSTRACT

Disclosed herein is a detector, comprising: a radiation absorption layer comprising an electric contact; a filter electrically connected to the electric contact and configured to attenuate signals from the electric contact below a first cutoff frequency; an integrator electrically connected to the filter and configured to integrate signals from the filter over a period of time.

24 Claims, 15 Drawing Sheets

(56) References Cited

FOREIGN PATENT DOCUMENTS

| | | | |
|---|---|---|---|
| CN | 107533146 | A | 1/2018 |
| CN | 107613871 | A | 1/2018 |
| CN | 107615095 | A | 1/2018 |
| CN | 108027448 | A | 5/2018 |
| CN | 108139488 | A | 6/2018 |
| CN | 108271415 | A | 7/2018 |
| EP | 0167119 | B1 | 10/1991 |
| JP | 2004362905 | A | 12/2004 |
| TW | 201816424 | A | 5/2018 |
| WO | 0065825 | A1 | 11/2000 |
| WO | 2016161542 | A1 | 10/2016 |
| WO | 2018076220 | A1 | 5/2018 |
| WO | 2018112721 | A1 | 6/2018 |

\* cited by examiner

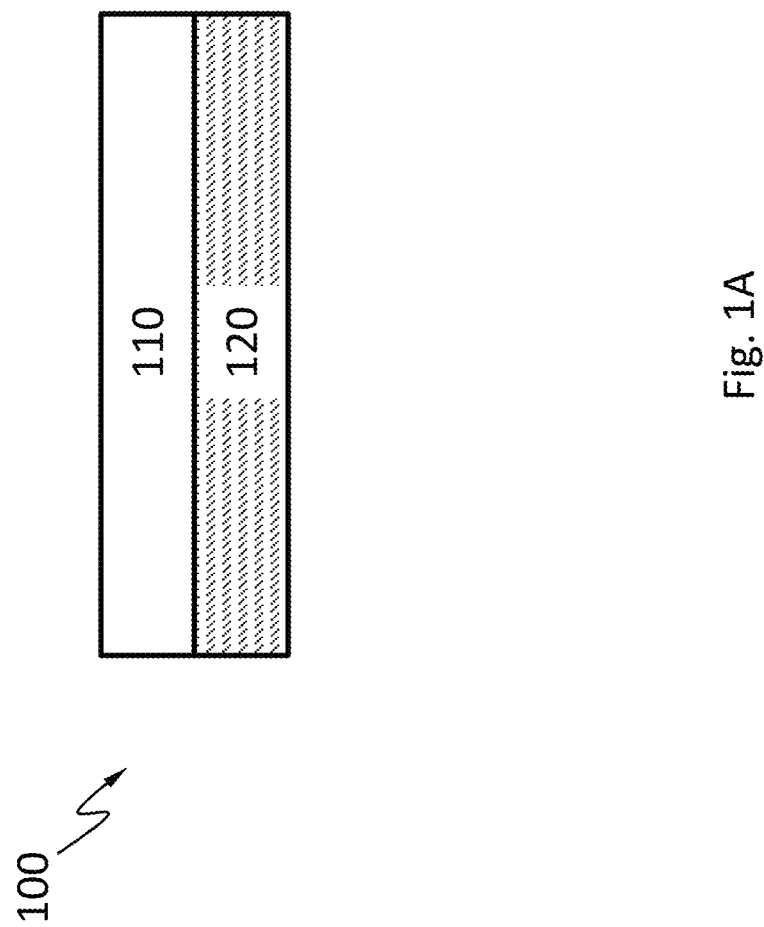

RADIATION DETECTOR

TECHNICAL FIELD

The disclosure herein relates to a radiation detector.

BACKGROUND

Radiation detectors may be devices used to measure the flux, spatial distribution, spectrum or other properties of radiations. Radiation detectors may be used for many applications. One important application is imaging. Radiation imaging is a radiography technique and can be used to reveal the internal structure of a non-uniformly composed and opaque object such as the human body.

Early radiation detectors for imaging include photographic plates and photographic films. A photographic plate may be a glass plate with a coating of light-sensitive emulsion. Although photographic plates were replaced by photographic films, they may still be used in special situations due to the superior quality they offer and their extreme stability. A photographic film may be a plastic film (e.g., a strip or sheet) with a coating of light-sensitive emulsion.

In the 1980s, photostimulable phosphor plates (PSP plates) became available. A PSP plate may contain a phosphor material with color centers in its lattice. When the PSP plate is exposed to radiation, electrons excited by radiation are trapped in the color centers until they are stimulated by a laser beam scanning over the plate surface. As the plate is scanned by laser, trapped excited electrons give off light, which is collected by a photomultiplier tube. The collected light is converted into a digital image. In contrast to photographic plates and photographic films, PSP plates can be reused.

Another kind of radiation detectors are radiation image intensifiers. Components of a radiation image intensifier are usually sealed in a vacuum. In contrast to photographic plates, photographic films, and PSP plates, radiation image intensifiers may produce real-time images, i.e., do not require post-exposure processing to produce images. radiation first hits an input phosphor (e.g., cesium iodide) and is converted to visible light. The visible light then hits a photocathode (e.g., a thin metal layer containing cesium and antimony compounds) and causes emission of electrons. The number of emitted electrons is proportional to the intensity of the incident radiation. The emitted electrons are projected, through electron optics, onto an output phosphor and cause the output phosphor to produce a visible-light image.

Scintillators operate somewhat similarly to radiation image intensifiers in that scintillators (e.g., sodium iodide) absorb radiation and emit visible light, which can then be detected by a suitable image sensor for visible light. In scintillators, the visible light spreads and scatters in all directions and thus reduces spatial resolution. Reducing the scintillator thickness helps to improve the spatial resolution but also reduces absorption of radiation. A scintillator thus has to strike a compromise between absorption efficiency and resolution.

Semiconductor radiation detectors largely overcome this problem by direct conversion of radiation into electric signals. A semiconductor radiation detector may include a semiconductor layer that absorbs radiation in wavelengths of interest. When a radiation particle is absorbed in the semiconductor layer, multiple charge carriers (e.g., electrons and holes) are generated and swept under an electric field towards electric contacts on the semiconductor layer.

SUMMARY

Disclosed herein is a detector, comprising: a radiation absorption layer comprising an electric contact; a filter electrically connected to the electric contact and configured to attenuate signals from the electric contact below a first cutoff frequency; an integrator electrically connected to the filter and configured to integrate signals from the filter over a period of time.

According to an embodiment, the filter is further configured to attenuate the signals from the electric contact between a second cutoff frequency and a third cutoff frequency.

According to an embodiment, the second cutoff frequency and the third cutoff frequency are both higher than the first cutoff frequency.

According to an embodiment, the radiation absorption layer is configured to generate charge carriers from radiation particles incident thereon, and the electric contact is configured to collect a portion of the charge carriers.

According to an embodiment, the radiation absorption layer comprises GaAs.

According to an embodiment, the radiation absorption layer produces a first component of dark noise, wherein the first component of dark noise is below the first cutoff frequency.

According to an embodiment, the radiation absorption layer produces a second component of dark noise, wherein the second component of dark noise is between the second cutoff frequency and the third cutoff frequency.

According to an embodiment, the radiation absorption layer comprises a first plurality of electric contacts and is configured to generate electrical signals on the first plurality of electric contacts from radiation incident on the radiation absorption layer; wherein the detector further comprises an electronics layer comprising a second plurality of electric contacts and an electronic system, wherein the electronic system is electrically connected to the second plurality of electric contacts and is configured to process or interpret the electrical signals; wherein the detector further comprises a distribution layer configured to electrically connect the first plurality of electric contacts to the second plurality of electric contacts, wherein the radiation absorption layer or the electronics layer comprises the distribution layer; wherein the first plurality of electric contacts and the second plurality of electric contacts have different spatial distributions.

According to an embodiment, a number density of the first plurality of electric contacts is lower than a number density of the second plurality of electric contacts.

According to an embodiment, the radiation absorption layer comprises the distribution layer.

According to an embodiment, the distribution layer comprises a plurality of vias aligned and connected to the first plurality of electric contacts.

According to an embodiment, the distribution layer further comprises a plurality of conductive pads, wherein the vias are connected to the conductive pads.

According to an embodiment, the second plurality of electric contacts are bonded to the conductive pads.

According to an embodiment, the electronics layer comprises the distribution layer.

According to an embodiment, the distribution layer comprises a plurality of vias aligned and connected to the second plurality of electric contacts.

According to an embodiment, the distribution layer further comprises a plurality of conductive pads, wherein the vias are connected to the conductive pads.

According to an embodiment, the first plurality of electric contacts are bonded to the conductive pads.

According to an embodiment, the detector comprises a plurality of pixels arranged in an array.

Disclosed herein is a system comprising a detector described above, and a radiation source, wherein the system is configured to perform radiation radiography on human body, limb or teeth.

Disclosed herein is a cargo scanning or non-intrusive inspection (NII) system, comprising the detector described above, and a radiation source, wherein the cargo scanning or non-intrusive inspection (NII) system is configured to identify elements by energy dispersive analysis using radiation transmitted through an object inspected.

Disclosed herein is a cargo scanning or non-intrusive inspection (NII) system, comprising the detector described above, and a radiation source, or gamma ray source, wherein the cargo scanning or non-intrusive inspection (NII) system is configured to identify elements by energy dispersive analysis using backscattered radiation.

Disclosed herein is a full-body scanner system comprising the detector described above, and a radiation source, wherein the full-body scanner is configured to identify elements.

Disclosed herein is a computed tomography (CT) system comprising the detector of any of the above radiation detectors and a radiation source.

Disclosed herein is an electron microscope comprising the radiation detector of any of the above radiation detectors, an electron source and an electronic optical system.

BRIEF DESCRIPTION OF FIGURES

FIG. 1A schematically shows a cross-sectional view of the radiation detector, according to an embodiment.

DETAILED DESCRIPTION

FIG. 1A schematically shows a cross-sectional view of a detector 100, according to an embodiment. The detector 100 may include a radiation absorption layer 110 and an electronics layer 120 (e.g., an ASIC) for processing or analyzing electrical signals incident radiation generates in the radiation absorption layer 110. In an embodiment, the detector 100 does not comprise a scintillator. The radiation absorption layer 110 may include a semiconductor such as GaAs. The semiconductor may have a high mass attenuation coefficient for the radiation energy of interest.

Figure 1B:
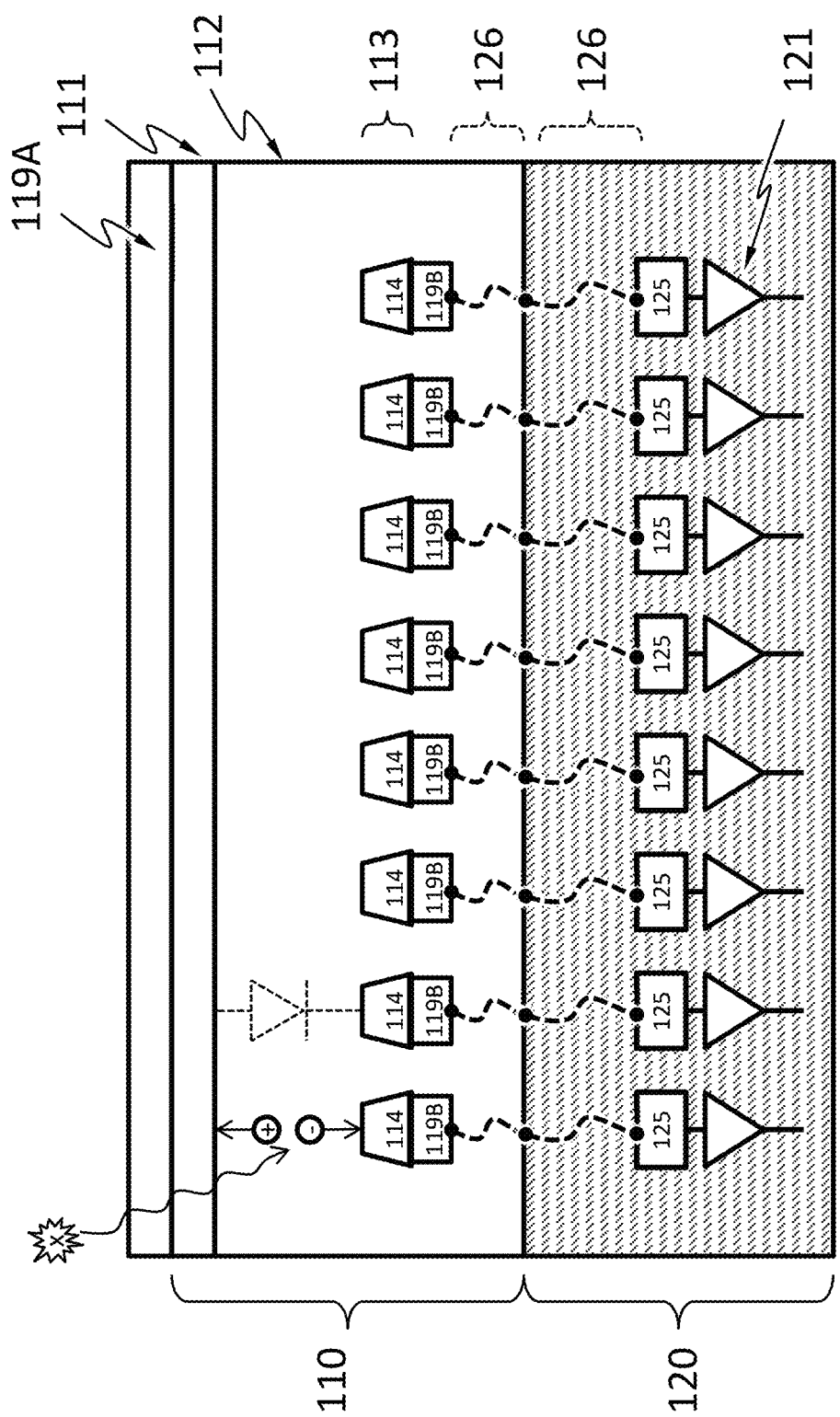
FIG. 1B schematically shows a detailed cross-sectional view of the radiation absorption layer and the electronics layer and their connection, according to an embodiment.

As shown in a detailed cross-sectional view of the detector 100 in FIG. 1B, according to an embodiment, the radiation absorption layer 110 may comprise an electric contact 119A, a first plurality of electric contacts 119B and one or more diodes (e.g., p-i-n or p-n) formed by a first doped region 111, one or more discrete regions 114 of a second doped region 113. The second doped region 113 may be separated from the first doped region 111 by an optional the intrinsic region 112. The discrete regions 114 are separated from one another by the first doped region 111 or the intrinsic region 112. The first doped region 111 and the second doped region 113 have opposite types of doping (e.g., region 111 is p-type and region 113 is n-type, or region 111 is n-type and region 113 is p-type). In the example in FIG. 1B, each of the discrete regions 114 of the second doped region 113 forms a diode with the first doped region 111 and the optional intrinsic region 112. Namely, in the example in FIG. 1B, the radiation absorption layer 110 has a plurality of diodes having the first doped region 111 as a shared electrode. The first doped region 111 may also have discrete portions. In the example in FIG. 1B, the electric contact 119A is shared among the diodes. The electric contact 119A may also have discrete portions. The first plurality of electric contacts 119B are in electric contact with the discrete regions 114.

When a radiation particle hits the radiation absorption layer 110 including diodes, the radiation particle may be absorbed and generate one or more charge carriers by a number of mechanisms. A radiation particle may generate 10 to 100000 charge carriers. The charge carriers may drift to the electrodes of one of the diodes under an electric field and generate electrical signals on the electric contacts 119A and 119B. The field may be an external electric field. In an embodiment, the charge carriers may drift in directions such that the charge carriers generated by a single radiation particle are not substantially shared by two different discrete regions 114 ("not substantially shared" here means less than 2%, less than 0.5%, less than 0.1%, or less than 0.01% of these charge carriers flow to a different one of the discrete regions 114 than the rest of the charge carriers). Charge carriers generated by a radiation particle incident around the footprint of one of these discrete regions 114 are not substantially shared with another of these discrete regions 114.

Figure 1C:
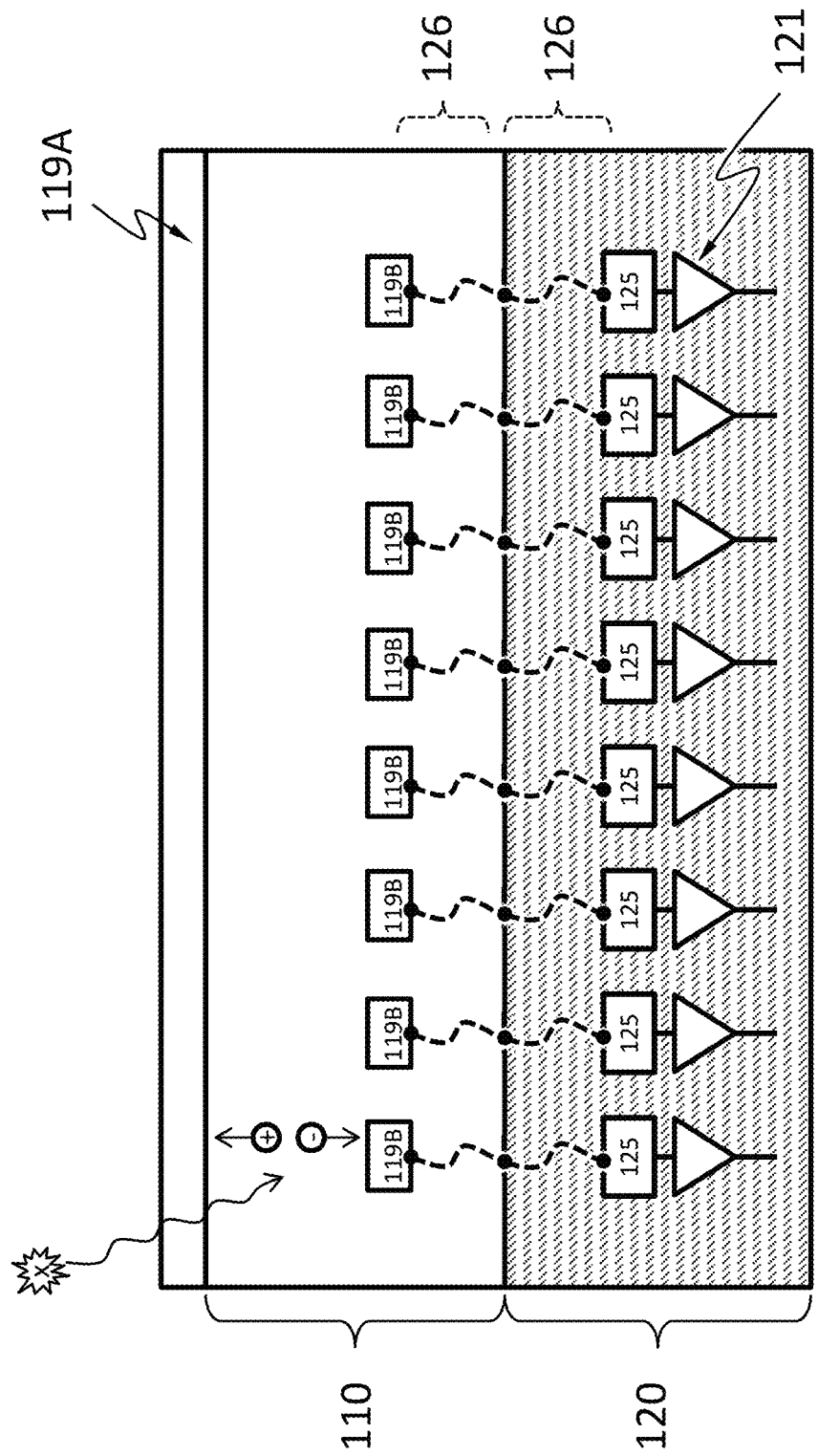
FIG. 1C schematically shows an alternative detailed cross-sectional view of the radiation absorption layer and the electronics layer and their connection, according to an embodiment.

As shown in an alternative detailed cross-sectional view of the detector 100 in FIG. 1C, according to an embodiment, the radiation absorption layer 110 may include a resistor of a semiconductor such as GaAs, but does not include a diode. The semiconductor may have a high mass attenuation coefficient for the radiation energy of interest.

When a radiation particle hits the radiation absorption layer 110 including a resistor but not diodes, it may be absorbed and generate one or more charge carriers by a number of mechanisms. A radiation particle may generate 10 to 100000 charge carriers. The charge carriers may drift to the electric contact 119A and the first plurality of electric contacts 119B under an electric field. The field may be an external electric field. In an embodiment, the charge carriers may drift in directions such that the charge carriers generated by a single radiation particle are not substantially shared by two different electric contacts of the first plurality of electric contacts 119B ("not substantially shared" here means less than 2%, less than 0.5%, less than 0.1%, or less than 0.01% of these charge carriers flow to a different one of the discrete portions than the rest of the charge carriers). Charge carriers generated by a radiation particle incident around the footprint of one of the first plurality of electric contacts 119B are not substantially shared with another of these first plurality of electric contacts 119B.

The electronics layer 120 may include an electronic system 121 suitable for processing or interpreting signals generated by radiation particles incident on the radiation absorption layer 110. The electronics layer 120 may comprise a second plurality of electric contacts 125 connecting to the electronic system 121. The electronic system 121 may include an analog circuitry such as a filter network, amplifiers, integrators, and comparators, or a digital circuitry such as a microprocessor, and a memory. The electronic system 121 may include components dedicated to each of the second plurality of electric contacts 125 or components shared by the second plurality of electric contacts 125.

In an embodiment, the spatial distribution of the first plurality of electric contacts 119B on the radiation absorption layer 110 may differ from the spatial distribution of the second plurality of electric contacts 125 on the electronics layer 120. For example, the first plurality of electric contacts 119B has a number density lower than the number density of the second plurality of electric contacts 125. In an embodiment, the radiation absorption layer 110 or the electronics layer 120 may comprise a distribution layer 126 configured to electrically connect the first plurality of electric contacts 119B to the second plurality of electric contacts 125.

Figure 2:
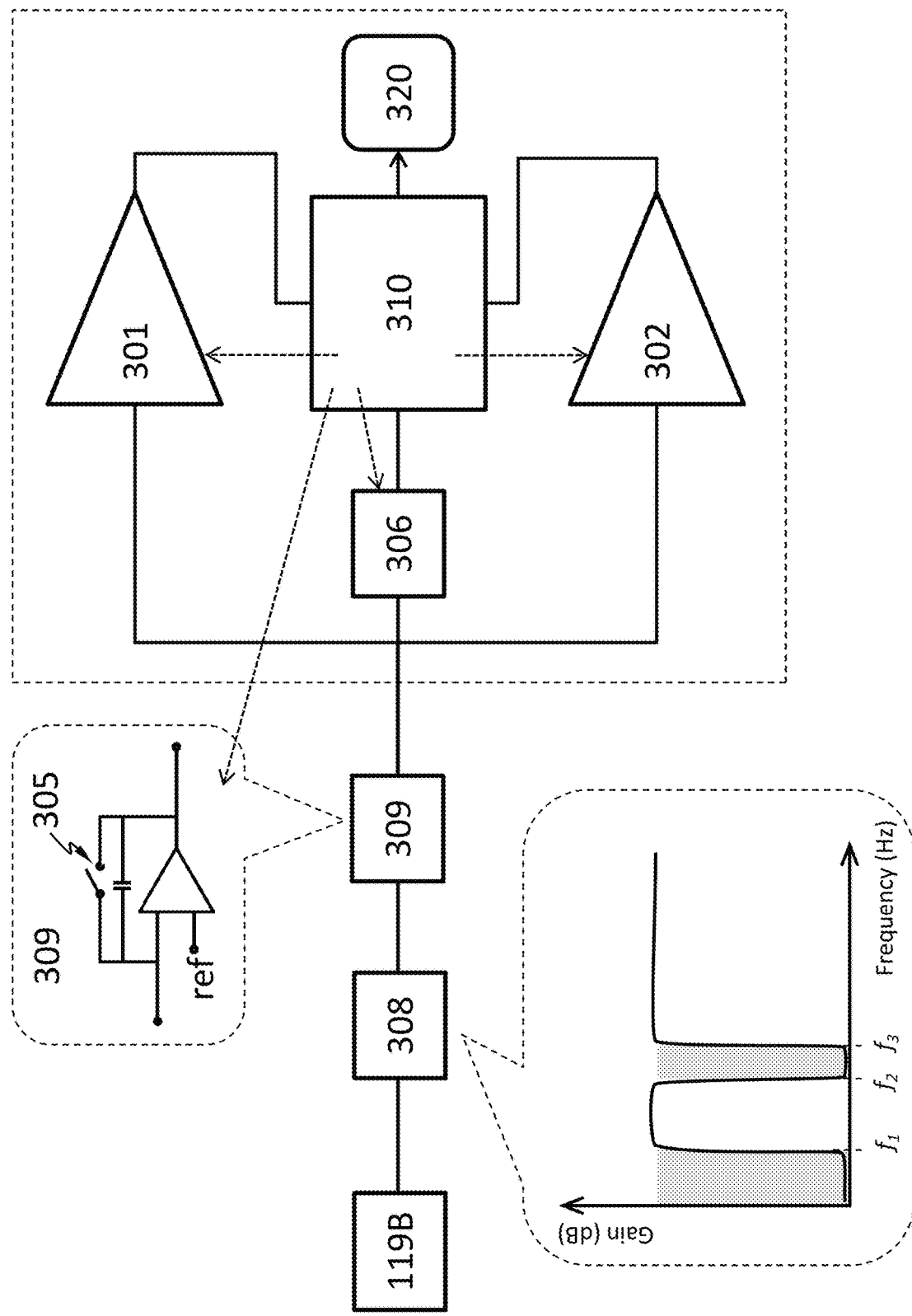
FIG. 2 schematically shows a functional block diagram of the electronic system of the radiation detector, according to an embodiment.

FIG. 2 each show a functional block diagram of the electronic system 121, according to an embodiment. The electronic system 121 may include a first voltage comparator 301, a second voltage comparator 302, a memory 320, a voltmeter 306, a filter 308, an integrator 309, and a controller 310.

The filter 308 is electrically connected to one or more electric contacts 119B. The filter 308 may comprise a high-pass filter, which is configured to attenuate electrical signals with frequencies below a first cutoff frequency $f_1$. The electrical signals with frequencies lower than the first cutoff frequency $f_1$ may be partially attributed to dark noise in the radiation absorption layer 110, or partially attributed to defects in the radiation absorption layer 110. Examples of the first cutoff frequency $f_1$ may include 1 MHz, 0.1 MHz, 10 KHz or 1 KHz.

The filter 308 may comprise a band rejection filter, which is configured to attenuate electrical signals with frequencies between a second cutoff frequency $f_2$ and a third cutoff frequency $f_3$. In an embodiment, the second cutoff frequency $f_2$ and the third cutoff frequency $f_3$ are both higher than the first cutoff frequency $f_1$. The electrical signals with frequencies between the second cutoff frequency $f_2$ and the third cutoff frequency $f_3$ may be partially attributed to defects in the radiation absorption layer 110 or other mechanisms.

Figure 3:
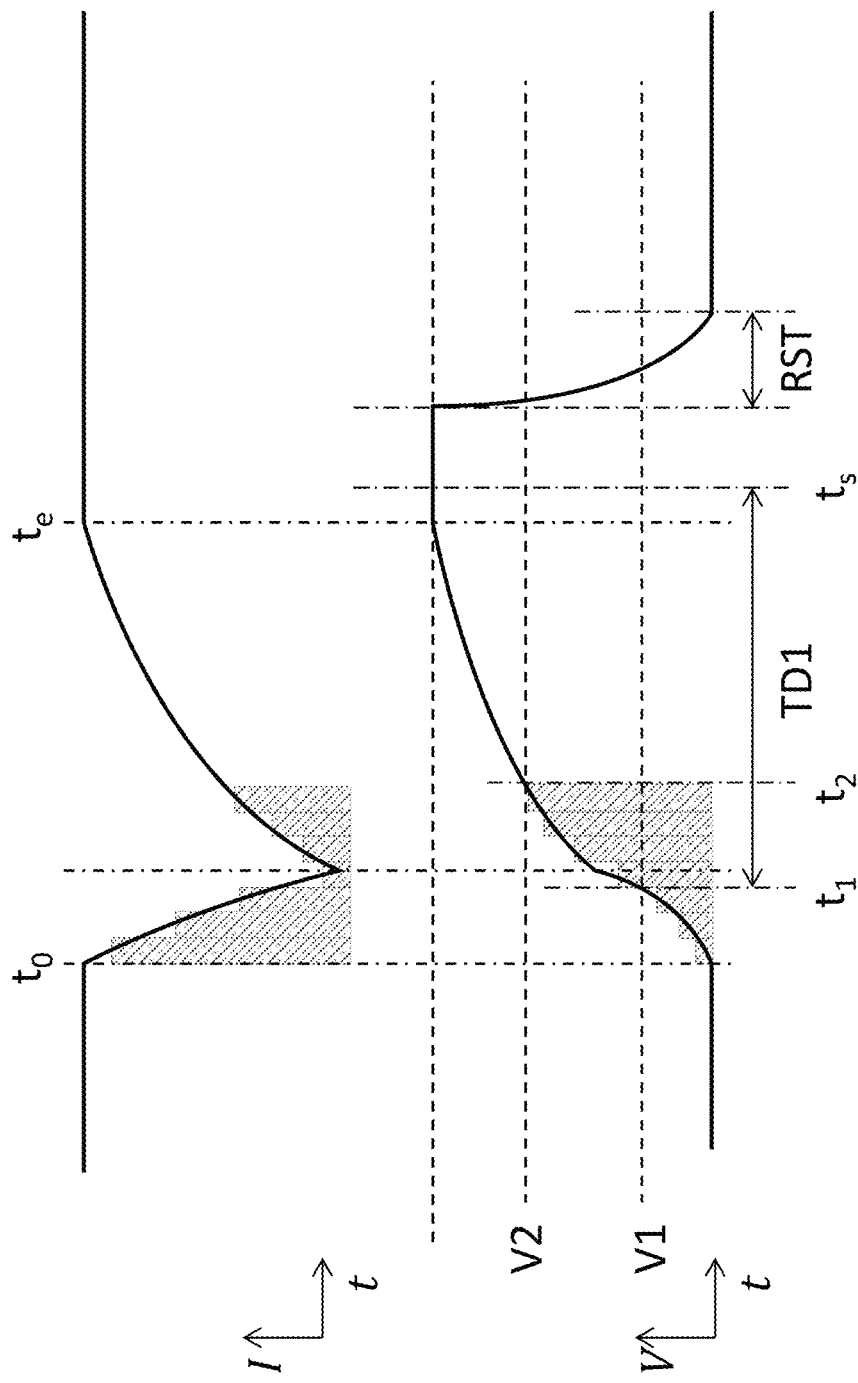
FIG. 3 schematically shows a temporal change of the electric current flowing through an electric contact (upper curve) of a diode of a radiation absorption layer exposed to radiation, the electric current caused by charge carriers generated by radiation particles incident on the radiation absorption layer, and a corresponding temporal change of the voltage of the electric contact (lower curve), according to an embodiment.

The integrator 309 may include an operational amplifier with a capacitor feedback loop (e.g., between the inverting input and the output of the operational amplifier). The integrator 309 is electrically connected to the filter 308 and is configured to integrate electrical signals from the filter 308 over a period time. The integrator 309 configured as shown in FIG. 2 is called a capacitive transimpedance amplifier (CTIA). CTIA has high dynamic range by keeping the amplifier from saturating and improves the signal-to-noise ratio by limiting the bandwidth in the signal path. Electrical signals from the filter 308 accumulate on the capacitor and are integrated over a period of time ("integration period") (e.g., as shown in FIG. 3, between $t_0$ to $t_1$, or $t_1$-$t_2$). After the integration period has expired, the voltage across the capacitor may be sampled and converted to digital signals by an ADC converter and then the capacitor is reset by a reset switch 305. The voltage may be measured by the voltmeter 306.

The first voltage comparator 301 is configured to compare the voltage across the capacitor to a first threshold. The first voltage comparator 301 may be controllably activated or deactivated by the controller 310. The first voltage comparator 301 may be a continuous comparator. Namely, the first voltage comparator 301 may be configured to monitor the voltage continuously. The first voltage comparator 301 configured as a continuous comparator reduces the chance that the system 121 misses signals generated by an incident radiation particle. The first voltage comparator 301 configured as a continuous comparator is especially suitable when the incident radiation intensity is relatively high. The first voltage comparator 301 may be a clocked comparator, which has the benefit of lower power consumption. The first voltage comparator 301 configured as a clocked comparator may cause the system 121 to miss signals generated by some incident radiation particles. When the incident radiation intensity is low, the chance of missing an incident radiation particle is low because the time interval between two successive radiation particles is relatively long. Therefore, the first voltage comparator 301 configured as a clocked comparator is especially suitable when the incident radiation intensity is relatively low. The first threshold may be 5-10%, 10%-20%, 20-30%, 30-40% or 40-50% of the maximum voltage one incident radiation particle may generate in the diode or the resistor. The maximum voltage may depend on the energy of the incident radiation particle (i.e., the wavelength of the incident radiation), the material of the radiation absorption layer 110, and other factors. For example, the first threshold may be 50 mV, 100 mV, 150 mV, or 200 mV.

The second voltage comparator 302 is configured to compare the voltage to a second threshold. The second voltage comparator 302 may be a continuous comparator. The second voltage comparator 302 may be controllably activate or deactivated by the controller 310. When the second voltage comparator 302 is deactivated, the power consumption of the second voltage comparator 302 may be less than 1%, less than 5%, less than 10% or less than 20% of the power consumption when the second voltage comparator 302 is activated. The absolute value of the second threshold is greater than the absolute value of the first threshold. As used herein, the term "absolute value" or "modulus" |x| of a real number x is the non-negative value $$|x| = \begin{cases} x, & \text{if } x \geq 0 \\ -x, & \text{if } x \leq 0 \end{cases}.$$

of x without regard to its sign. Namely, The second threshold may be 200%-300% of the first threshold. The second threshold may be at least 50% of the maximum voltage one incident radiation particle may generate in the diode or resistor. For example, the second threshold may be 100 mV, 150 mV, 200 mV, 250 mV or 300 mV. The second voltage comparator 302 and the first voltage comparator 310 may be the same component. Namely, the electric system 121 may have one voltage comparator that can compare a voltage with two different thresholds at different times.

The first voltage comparator 301 or the second voltage comparator 302 may include one or more op-amps or any other suitable circuitry. The first voltage comparator 301 or the second voltage comparator 302 may have a high speed to allow the electronic system 121 to operate under a high flux of incident radiation. However, having a high speed is often at the cost of power consumption.

The memory 320 is configured to store a number of the radiation particles incident on the radiation absorption layer 110.

The controller 310 may be a hardware component such as a microcontroller and a microprocessor. The controller 310 is configured to start a time delay from a time at which the first voltage comparator 301 determines that the absolute value of the voltage equals or exceeds the absolute value of the first threshold (e.g., the absolute value of the voltage increases from below the absolute value of the first threshold to a value equal to or above the absolute value of the first threshold). The absolute value is used here because the voltage may be negative or positive, depending on whether the voltage of the cathode or the anode of the diode or which electric contact is used. The controller 310 may be configured to keep deactivated the second voltage comparator 302, the memory 320 and any other circuits the operation of the first voltage comparator 301 does not require, before the time at which the first voltage comparator 301 determines that the absolute value of the voltage equals or exceeds the absolute value of the first threshold. The time delay may expire before or after the voltage becomes stable, i.e., the rate of change of the voltage is substantially zero. The phase "the rate of change of the voltage is substantially zero" means that temporal change of the voltage is less than 0.1%/ns. The phase "the rate of change of the voltage is substantially non-zero" means that temporal change of the voltage is at least 0.1%/ns.

The controller 310 may be configured to activate the second voltage comparator during (including the beginning and the expiration) the time delay. In an embodiment, the controller 310 is configured to activate the second voltage comparator at the beginning of the time delay. The term "activate" means causing the component to enter an operational state (e.g., by sending a signal such as a voltage pulse or a logic level, by providing power, etc.). The term "deactivate" means causing the component to enter a non-operational state (e.g., by sending a signal such as a voltage pulse or a logic level, by cut off power, etc.). The operational state may have higher power consumption (e.g., 10 times higher, 100 times higher, 1000 times higher) than the non-operational state. The controller 310 itself may be deactivated until the output of the first voltage comparator 301 activates the controller 310 when the absolute value of the voltage equals or exceeds the absolute value of the first threshold.

The controller 310 may be configured to determine that a radiation particle is absorbed by the radiation absorption layer 110 and cause the number of the radiation particles registered by the memory 320 to increase by one, when, during the time delay, the second voltage comparator 302 determines that the absolute value of the voltage equals or exceeds the absolute value of the second threshold.

The controller 310 may be configured to cause the voltmeter 306 to measure the voltage upon expiration of the time delay. The controller 310 may be configured to connect the electric contact 119B to an electrical ground, so as to reset the voltage and discharge any charge carriers accumulated on the electric contact 119B. In an embodiment, the electric contact 119B is connected to an electrical ground after the expiration of the time delay. In an embodiment, the electric contact 119B is connected to an electrical ground for a finite reset time period. The controller 310 may connect the electric contact 119B to the electrical ground by controlling the switch 305. The switch may be a transistor such as a field-effect transistor (FET).

In an embodiment, the electric system 121 has no analog filter network (e.g., a RC network).

The voltmeter 306 may feed the value of the voltage it measures to the controller 310 as an analog or digital signal.

FIG. 3 schematically shows a temporal change (upper curve) of the electric current flowing from the electric contact 119B to the filter 308, the electric current caused by charge carriers generated by radiation particles incident on the diode or the resistor, and a corresponding temporal change of the voltage across the capacitor (lower curve). At time $t_0$, the radiation particle hits the diode or the resistor, charge carriers start being generated in radiation absorption layer 110, electric current starts to flow from the electric contact 119B, and the electrical signals passed by the filter 308 may be integrated by the integrator 309 over the integration period of time. At time $t_1$, the first voltage comparator 301 determines that the absolute value of the voltage equals or exceeds the absolute value of the first threshold V1, and the controller 310 starts the time delay TD1 and the controller 310 may deactivate the first voltage comparator 301 at the beginning of TD1. If the controller 310 is deactivated before $t_1$, the controller 310 is activated at $t_1$. During TD1, the controller 310 activates the second voltage comparator 302. The term "during" a time delay as used here means the beginning and the expiration (i.e., the end) and any time in between. For example, the controller 310 may activate the second voltage comparator 302 at the expiration of TD1. If during TD1, the second voltage comparator 302 determines that the absolute value of the voltage equals or exceeds the absolute value of the second threshold at time $t_2$, the controller 310 causes the number registered by the memory 320 to increase by one. At time $t_e$, all charge carriers generated by the radiation particles drift out of the radiation absorption layer 110. At time $t_s$, the time delay TD1 expires. In the example of FIG. 3, time $t_s$ is after time $t_e$; namely TD1 expires after all charge carriers generated by the radiation particles drift out of the radiation absorption layer 110. The rate of change of the voltage is thus substantially zero at $t_s$. The controller 310 may be configured to deactivate the second voltage comparator 302 at expiration of TD1 or at $t_2$, or any time in between.

The controller 310 may be configured to cause the voltmeter 306 to measure the voltage upon expiration of the time delay TD1. In an embodiment, the controller 310 causes the voltmeter 306 to measure the voltage after the rate of change of the voltage becomes substantially zero after the expiration of the time delay TD1. The voltage at this moment relates to the energy of the radiation particles. The controller 310 may be configured to determine the energy of the radiation particles based on the voltage.

After TD1 expires, the controller 310 connects the electric contact 119B to an electric ground for a reset period RST to allow charge carriers accumulated on the electric contact 119B to flow to the ground and reset the voltage. After RST, the system 121 is ready to detect next incident radiation particles. Implicitly, the rate of incident radiation particles the system 121 can handle in the example of FIG. 3 is limited by 1/(TD1+RST). If the first voltage comparator 301 has been deactivated, the controller 310 can activate it at any time before RST expires. If the controller 310 has been deactivated, it may be activated before RST expires.

Figure 4A:
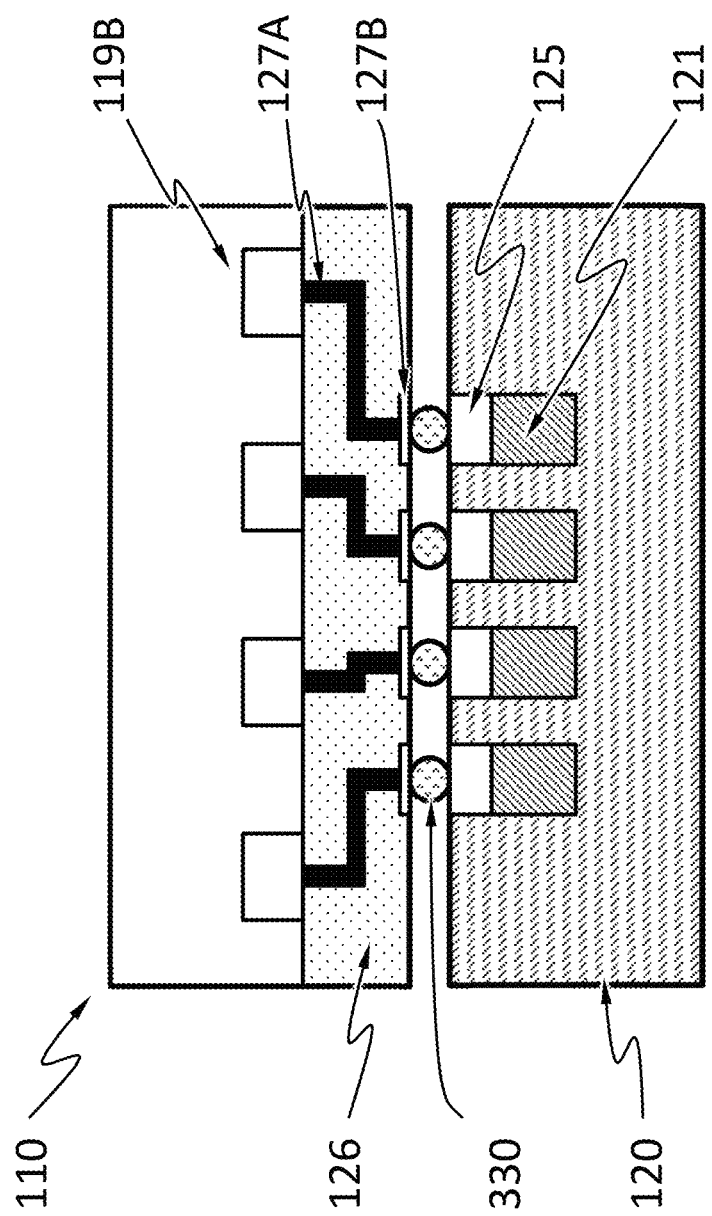
FIG. 4A and FIG. 4B each schematically shows a form of electrical connection between the electronics layer and the radiation absorption layer, according to an embodiment.

FIG. 4A schematically shows a detailed cross-sectional view of the detector 100, according to an embodiment, where the radiation absorption layer 110 comprises the distribution layer 126 (i.e., the distribution layer 126 is formed on the same substrate as the rest of the radiation absorption layer 110). The distribution layer 126 may comprise a plurality of vias 127A aligned and connected to the first plurality of electric contacts 119B. The distribution layer 126 may also comprise a plurality of conductive pads 127B connected to the vias 127A and bonded to the second plurality of electric contacts 125. The distribution layer 126 may have multiple alternating layers of vias 127A and connections in between. The vias 127A and conductive pads 127B may include electrically conductive materials such as copper and aluminum. The distribution layer 126 may comprise an electrically insulating material (e.g. silicon dioxide) in which the vias 127A and conductive pads 127B are embedded.

The bonding of the radiation absorption layer 110 to the electronics layer 120 may be by a suitable technique such as direct bonding, wire bonding or flip chip bonding.

Direct bonding is a wafer bonding process without any additional intermediate layers (e.g., solder bumps). The bonding process is based on chemical bonds between two surfaces. Direct bonding may be at elevated temperature but not necessarily so.

Wire bonding is a bonding process using wire bonds (e.g., gold wires and copper wires) to connect the radiation absorption layer 110 to the electronics layer 120. The wire bonds may be fixed and secured with an electrically insulating material such as epoxy.

Flip chip bonding uses solder bumps 330 deposited onto contact pads (e.g., the conductive pads 127B of the distribution layer 126). Either the radiation absorption layer 110 or the electronics layer 120 is flipped over and the contact pads of each layer are aligned. The solder bumps 330 may be melted to solder together the contact pads of the radiation absorption layer 110 and the electronics layer 120. Any void space among the solder bumps 330 may be filled with an insulating material.

Figure 4B:
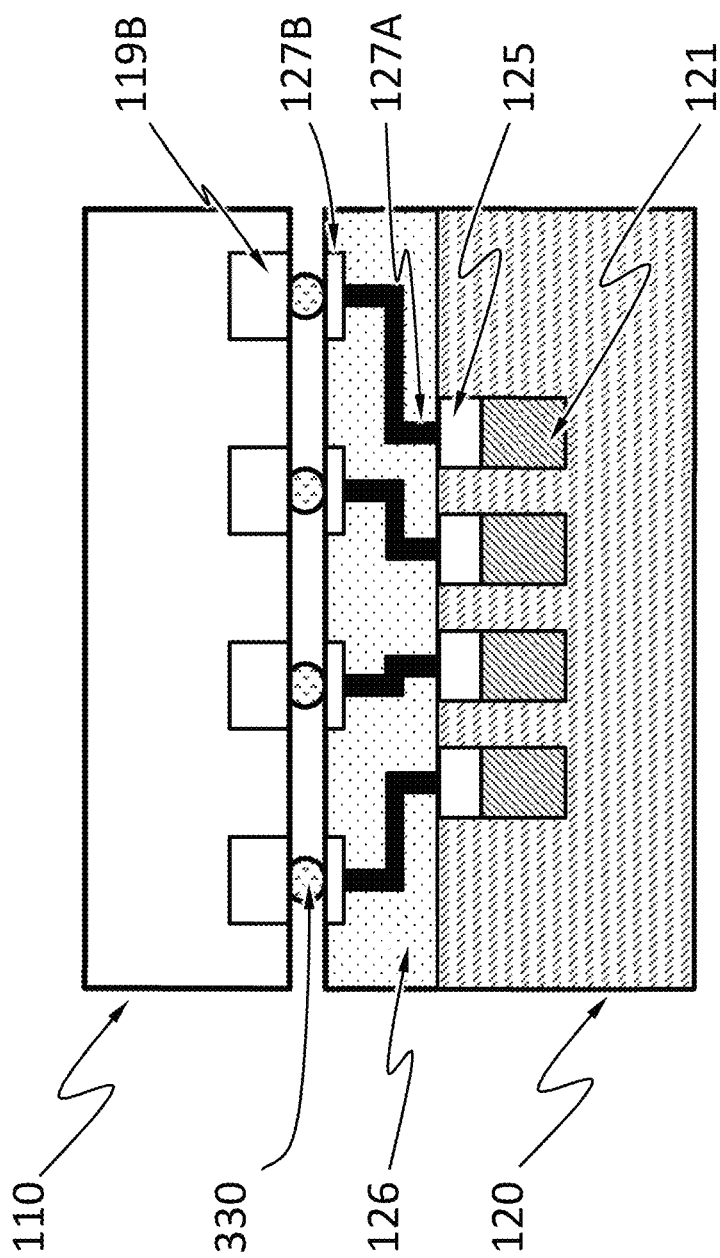

As shown in a detailed cross-sectional view of the detector 100 in FIG. 4B, according to an embodiment. The structure shown in FIG. 4B is similar to the structure in FIG. 4A expect that the electronics layer 120 comprises the distribution layer 126 (i.e., the distribution layer 126 is formed on the same substrate as the rest of the electronics layer 120). The distribution layer 126 may comprise a plurality of vias 127A aligned and connected to the second plurality of electric contacts 125. The distribution layer 126 may also comprise a plurality of conductive pads 127B connected to the vias 127A and bonded to the first plurality of electric contacts 119B.

Figure 5:
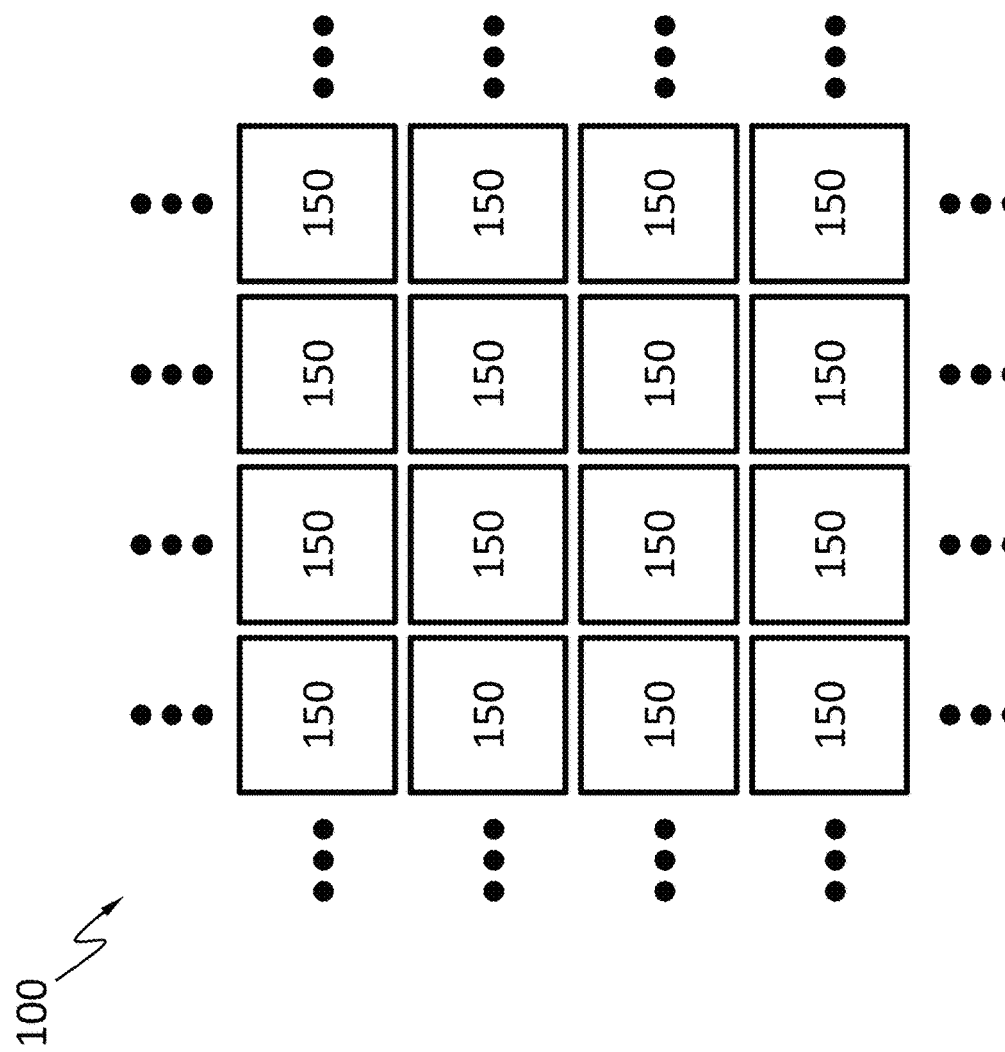
FIG. 5 schematically shows a top view of the radiation detector, according to an embodiment.

FIG. 5 schematically shows an exemplary top view of a portion of the detector 100, according to an embodiment. The detector 100 comprises a plurality of pixels 150 arranged in arrays, such as a rectangular array, a honeycomb array, a hexagonal array or any other suitable arrays. Each of the pixels 150 may have its own analog-to-digital converter (ADC) configured to digitize an analog signal representing the energy of an incident radiation particle into a digital signal. For some radiation detection applications, an ADC with a 10-bit resolution or higher is useful. Each of the pixels 150 may be configured to measure its dark current, such as before or concurrently with detection of each radiation particle incident thereon. Each of the pixels 150 may be configured to deduct the contribution of the dark current from the energy of the radiation particle incident thereon. The pixels 150 may be configured to operate in parallel. For example, when one of the pixels 150 measures an incident radiation particle, another one of the pixels 150 may be waiting for a radiation particle to arrive. The pixels 150 may not have to be individually addressable. Because the detector 100 has many pixels 150 that may operate in parallel, the detector can handle much higher rate of incident radiation particles. This is because the rate of incidence on a particular pixel 150 is 1/N of the rate of incidence on the entire array of pixels, where N is the number of pixels.

Figure 6:
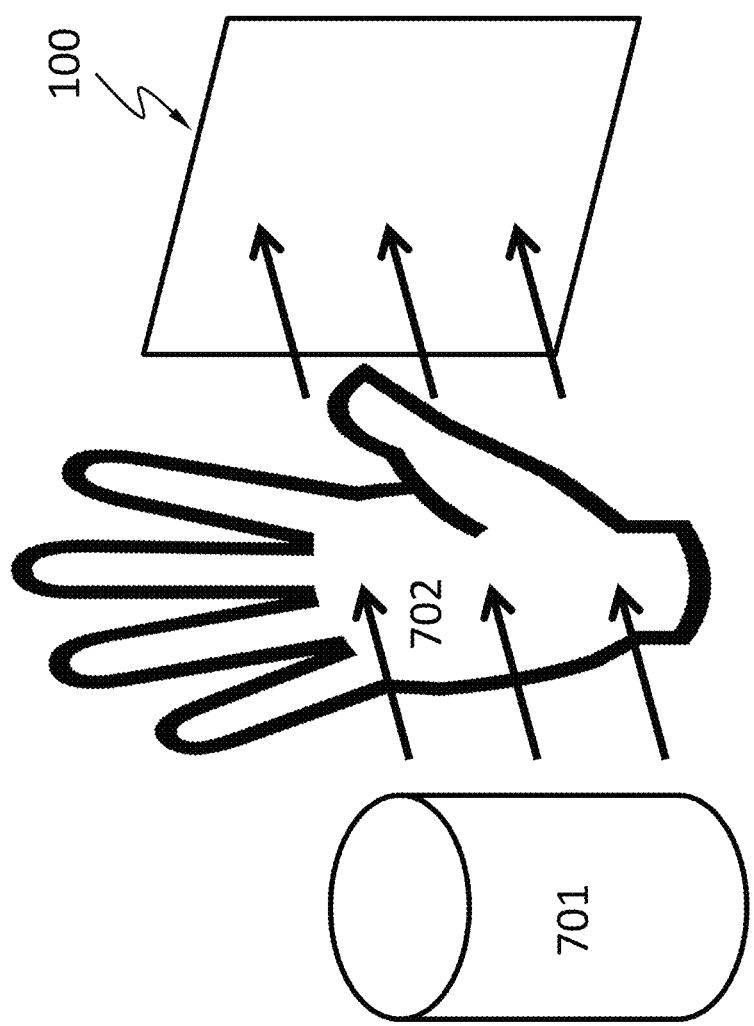
FIG. 6-FIG. 12 each schematically shows a system comprising the radiation detector described herein.

FIG. 6 schematically shows a system comprising the detector 100 described herein. The system may be used for medical imaging such as chest radiation radiography, abdominal radiation radiography, dental radiation radiography, etc. The system comprises a radiation source 701. radiation emitted from the radiation source 701 penetrates an object 702 (e.g., a human body part such as chest, limb, abdomen, mouth), is attenuated by different degrees by the internal structures of the object 702 (e.g., bones, muscle, fat, organs and teeth, etc.), and is projected to the detector 100. The detector 100 forms an image by detecting the intensity distribution of the radiation.

Figure 7:
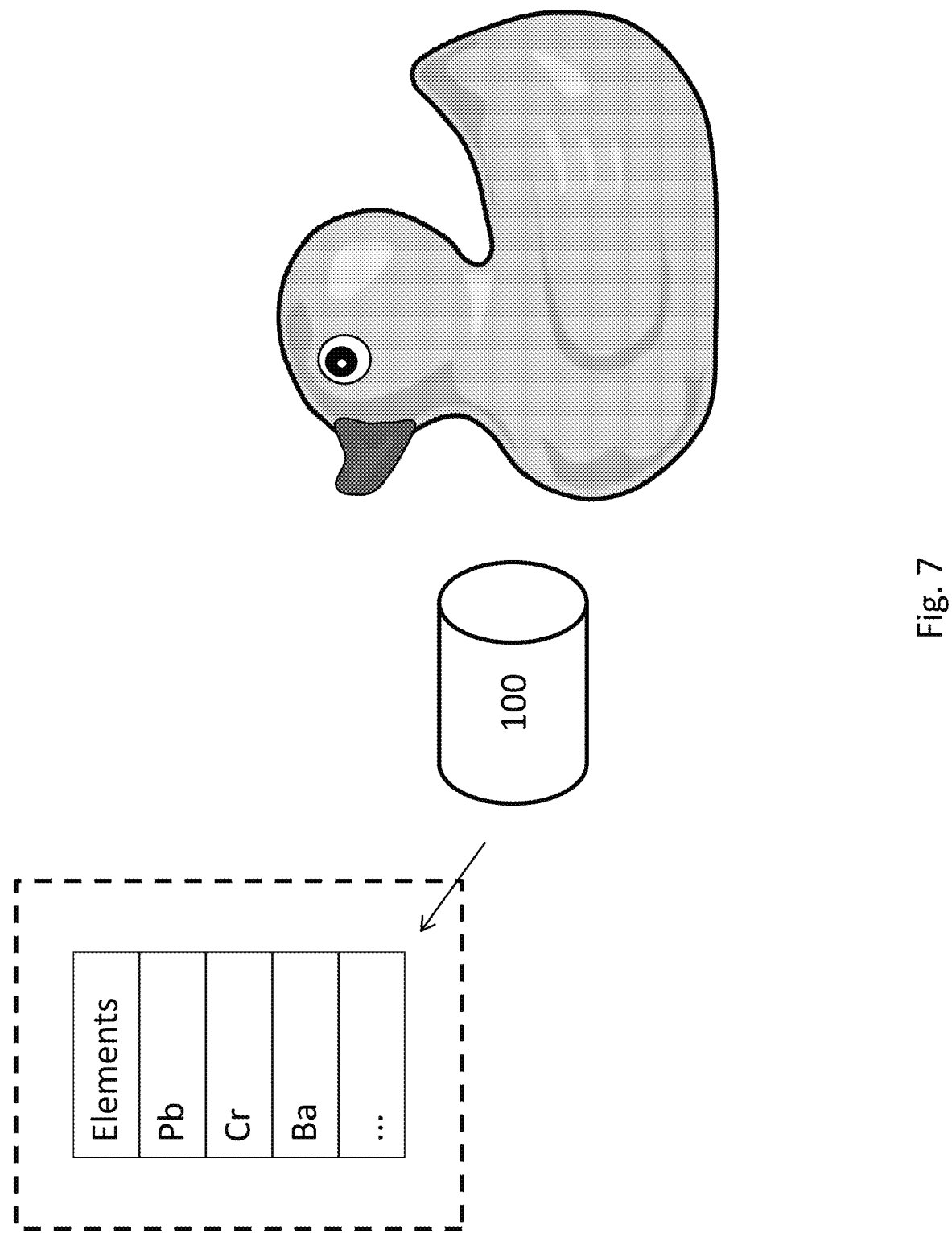

FIG. 7 schematically shows an element analyzer comprising the detector 100 described herein. The element analyzer measurer is capable of detecting presence of one or more elements of interest on an object such as a toy. A high-energy beam of charged particles such as electrons or protons, or a beam of radiations, is directed onto the object. Atoms of the objects are excited and emit radiation at specific wavelengths that are characteristic of the elements. The detector 100 receives the emitted radiation and determines the presence of the elements based on the energy of the emitted radiation. For example, the detector 100 may be configured to detect radiation at wavelengths Pb would emit. If the detector 100 actually receives radiation from the object at these wavelengths, it can tell that Pb is present. The detector 100 described here may have other applications such as in a radiation telescope, radiation mammography, industrial radiation defect detection, radiation microscopy or microradiography, radiation casting inspection, radiation non-destructive testing, radiation weld inspection, radiation digital subtraction angiography, etc. It may be suitable to use this detector 100 in place of a photographic plate, a photographic film, a PSP plate, a radiation image intensifier, a scintillator, or another radiation detector.

Figure 8:
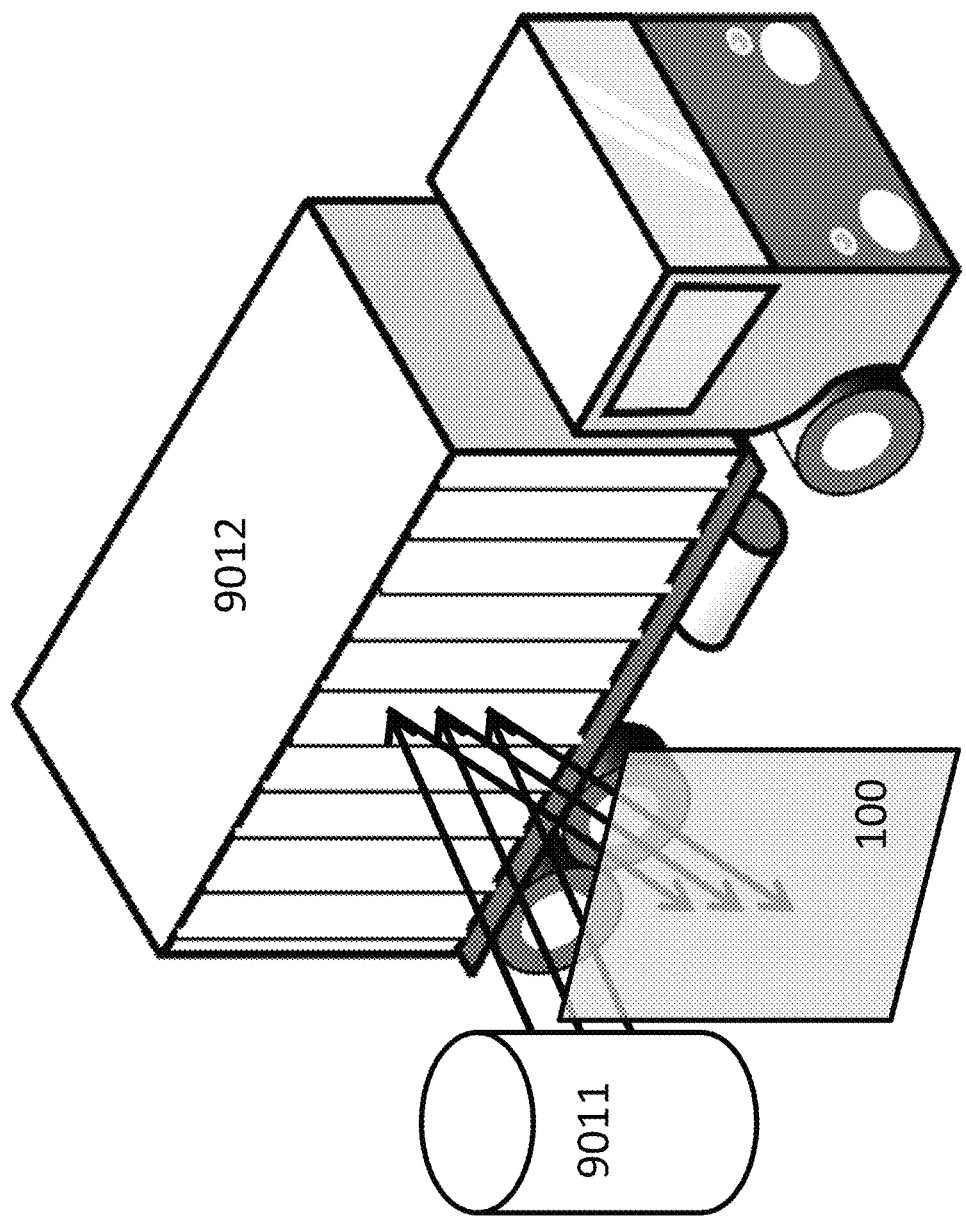

FIG. 8 schematically shows a cargo scanning or non-intrusive inspection (NII) system comprising the detector 100 described herein. The system may be used for inspecting and identifying goods in transportation systems such as shipping containers, vehicles, ships, luggage, etc. The system comprises a radiation source 9011. radiation emitted from the radiation source 9011 may backscatter from an object 9012 (e.g., shipping containers, vehicles, ships, etc.) and be projected to the detector 100. Different internal structures of the object 9012 may backscatter radiation differently. The detector 100 forms an image by detecting the intensity distribution of the backscattered radiation and/or energies of the backscattered radiation particles.

Figure 9:
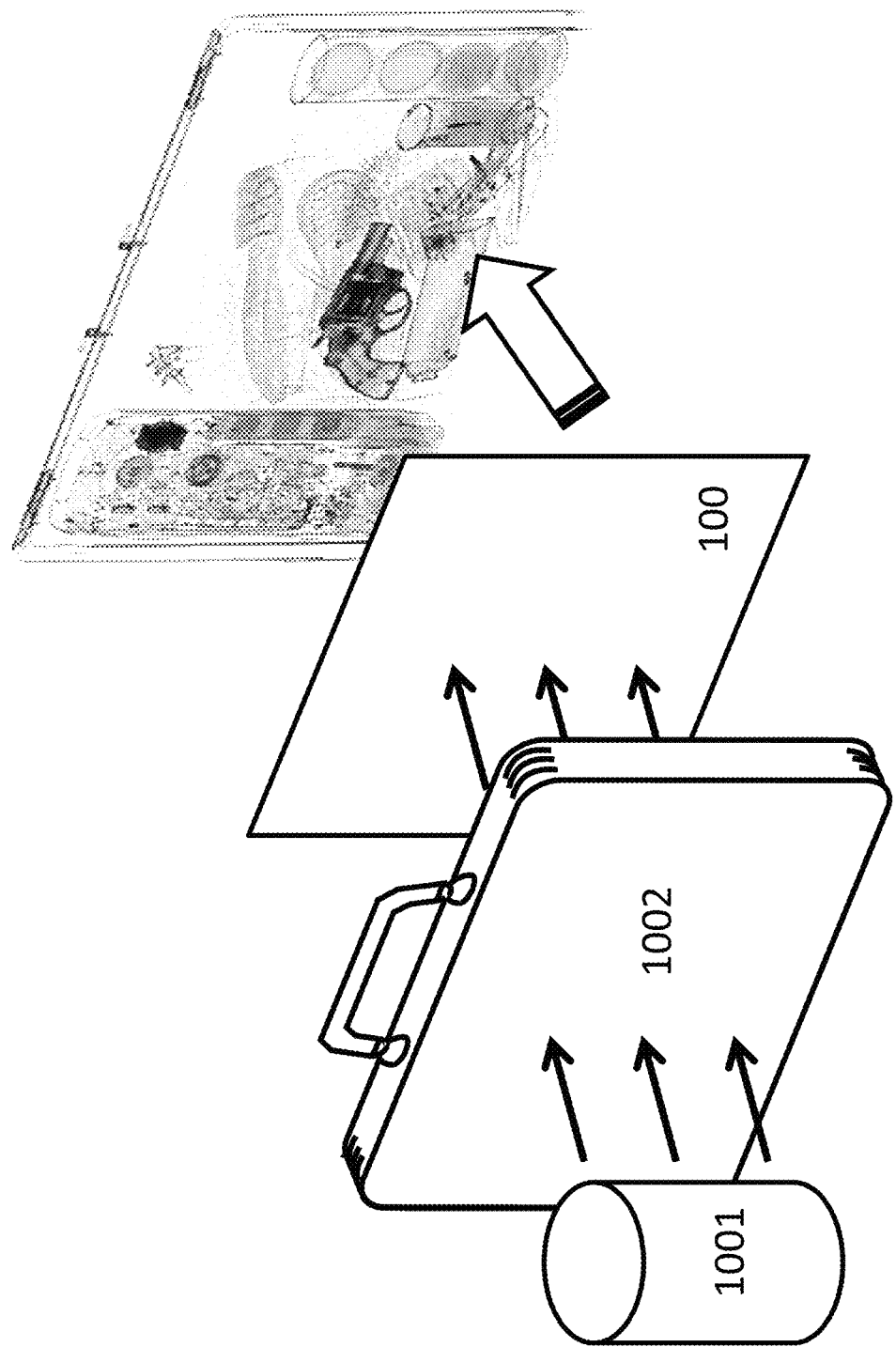

FIG. 9 schematically shows another cargo scanning or non-intrusive inspection (NII) system comprising the detector 100 described herein. The system may be used for luggage screening at public transportation stations and airports. The system comprises a radiation source 1001. radiation emitted from the radiation source 1001 may penetrate a piece of luggage 1002, be differently attenuated by the contents of the luggage, and projected to the detector 100. The detector 100 forms an image by detecting the intensity distribution of the transmitted radiation. The system may reveal contents of luggage and identify items forbidden on public transportation, such as firearms, narcotics, edged weapons, flammables.

Figure 10:
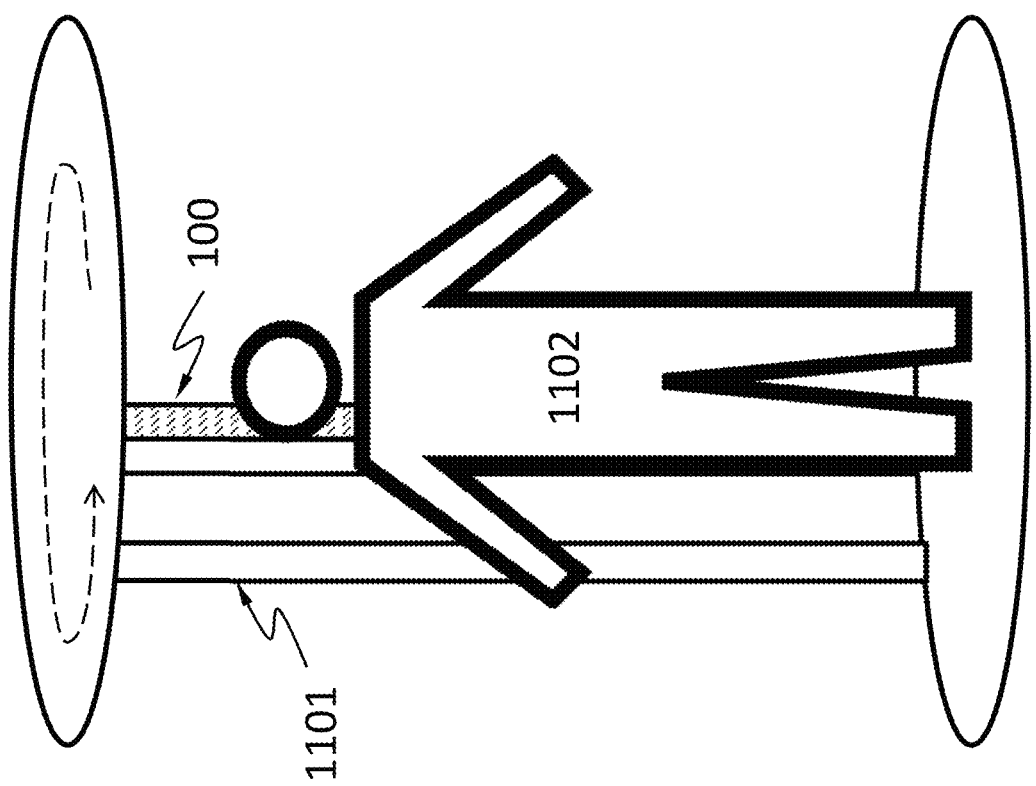

FIG. 10 schematically shows a full-body scanner system comprising the detector 100 described herein. The full-body scanner system may detect objects on a person's body for security screening purposes, without physically removing clothes or making physical contact. The full-body scanner system may be able to detect non-metal objects. The full-body scanner system comprises a radiation source 1101. radiation emitted from the radiation source 1101 may backscatter from a human 1102 being screened and objects thereon, and be projected to the detector 100. The objects and the human body may backscatter radiation differently. The detector 100 forms an image by detecting the intensity distribution of the backscattered radiation. The detector 100 and the radiation source 1101 may be configured to scan the human in a linear or rotational direction.

Figure 11:
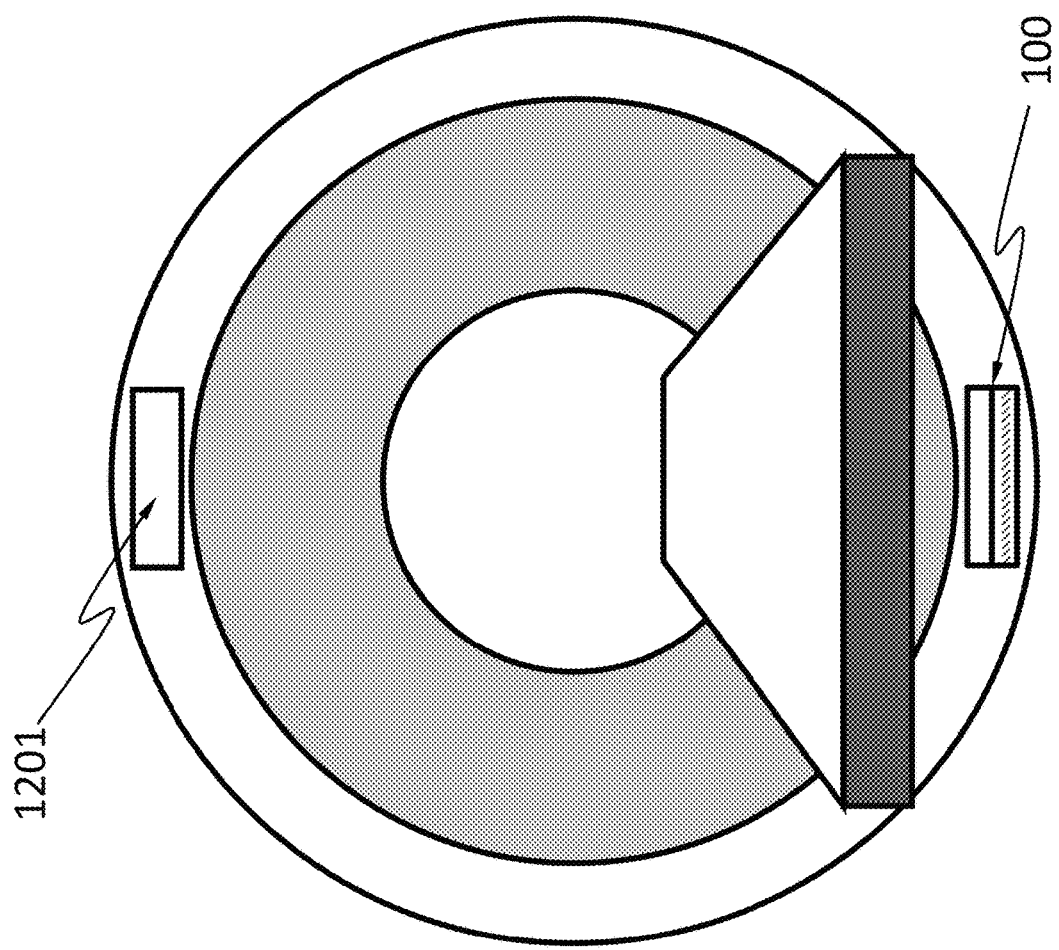

FIG. 11 schematically shows a radiation computed tomography (radiation CT) system comprising the detector 100 described herein. The radiation CT system uses computer-processed radiations to produce tomographic images (virtual "slices") of specific areas of a scanned object. The tomographic images may be used for diagnostic and therapeutic purposes in various medical disciplines, or for flaw detection, failure analysis, metrology, assembly analysis and reverse engineering. The radiation CT system comprises the detector 100 described herein and a radiation source 1201. The detector 100 and the radiation source 1201 may be configured to rotate synchronously along one or more circular or spiral paths.

Figure 12:
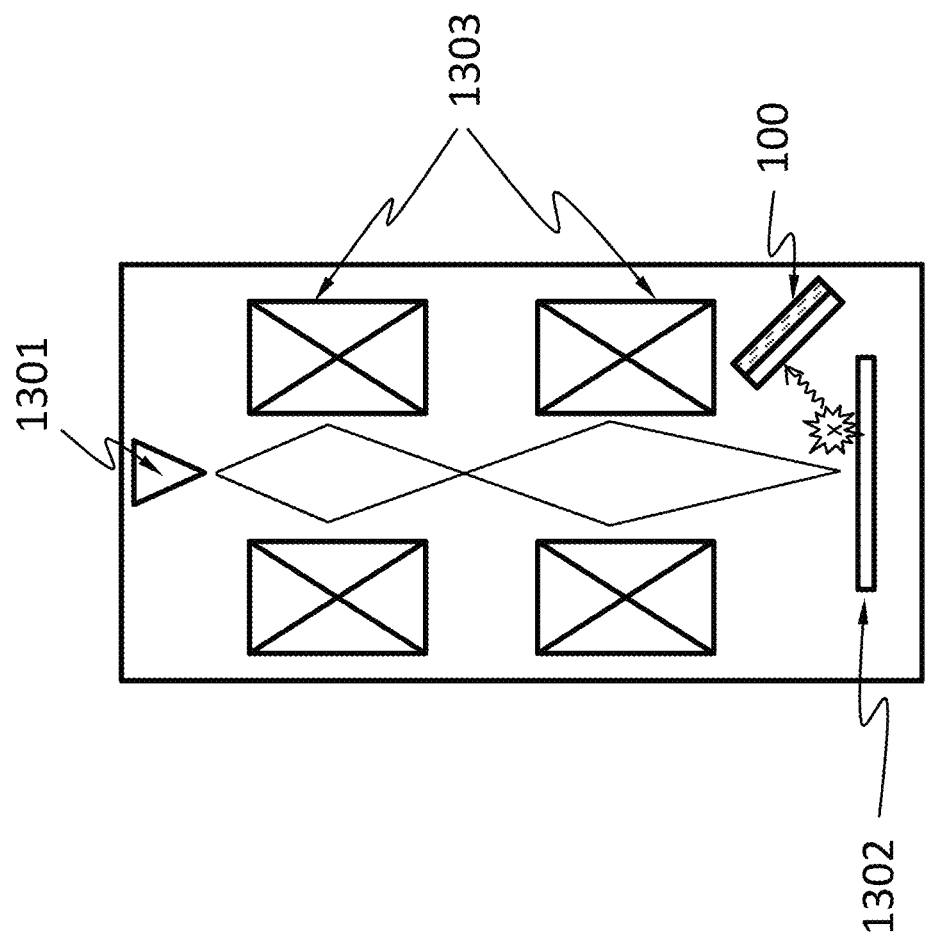

FIG. 12 schematically shows an electron microscope comprising the detector 100 described herein. The electron microscope comprises an electron source 1301 (also called an electron gun) that is configured to emit electrons. The electron source 1301 may have various emission mechanisms such as thermionic, photocathode, cold emission, or plasmas source. The emitted electrons pass through an electronic optical system 1303, which may be configured to shape, accelerate, or focus the electrons. The electrons then reach a sample 1302 and an image detector may form an image therefrom. The electron microscope may comprise the detector 100 described herein, for performing energy-dispersive radiation spectroscopy (EDS). EDS is an analytical technique used for the elemental analysis or chemical characterization of a sample. When the electrons incident on a sample, they cause emission of characteristic radiations from the sample. The incident electrons may excite an electron in an inner shell of an atom in the sample, ejecting it from the shell while creating an electron hole where the electron was. An electron from an outer, higher-energy shell then fills the hole, and the difference in energy between the higher-energy shell and the lower energy shell may be released in the form of a radiation. The number and energy of the radiations emitted from the sample can be measured by the detector 100.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

What is claimed is:

1. A detector comprising:
a radiation absorption layer comprising an electric contact;
a filter electrically connected to the electric contact and configured to attenuate signals from the electric contact below a first cutoff frequency;
an integrator electrically connected to the filter and configured to integrate signals from the filter over a period of time;
wherein the filter is further configured to attenuate the signals from the electric contact between a second cutoff frequency and a third cutoff frequency.

2. The detector of claim 1, wherein the second cutoff frequency and the third cutoff frequency are both higher than the first cutoff frequency.

3. The detector of claim 1, wherein the radiation absorption layer is configured to generate charge carriers from radiation particles incident thereon, and the electric contact is configured to collect a portion of the charge carriers.

4. The detector of claim 1, wherein the radiation absorption layer comprises GaAs.

5. The detector of claim 1, wherein the radiation absorption layer produces a first component of dark noise, wherein the first component of dark noise is below the first cutoff frequency.

6. The detector of claim 1, wherein the radiation absorption layer produces a second component of dark noise, wherein the second component of dark noise is between the second cutoff frequency and the third cutoff frequency.

7. The detector of claim 1,
wherein the radiation absorption layer comprises a first plurality of electric contacts and is configured to generate electrical signals on the first plurality of electric contacts from radiation incident on the radiation absorption layer;
wherein the detector further comprises an electronics layer comprising a second plurality of electric contacts and an electronic system, wherein the electronic system is electrically connected to the second plurality of electric contacts and is configured to process or interpret the electrical signals;
wherein the detector further comprises a distribution layer configured to electrically connect the first plurality of electric contacts to the second plurality of electric contacts, wherein the radiation absorption layer or the electronics layer comprises the distribution layer;
wherein the first plurality of electric contacts and the second plurality of electric contacts have different spatial distributions.

8. The detector of claim 7, wherein a number density of the first plurality of electric contacts is lower than a number density of the second plurality of electric contacts.

9. The detector of claim 7, wherein the radiation absorption layer comprises the distribution layer.

10. The detector of claim 9, wherein the distribution layer comprises a plurality of vias aligned and connected to the first plurality of electric contacts.

11. The detector of claim 10, wherein the distribution layer further comprises a plurality of conductive pads, wherein the vias are connected to the conductive pads.

12. The detector of claim 11, wherein the second plurality of electric contacts are bonded to the conductive pads.

13. The detector of claim 7, wherein the electronics layer comprises the distribution layer.

14. The detector of claim 13, wherein the distribution layer comprises a plurality of vias aligned and connected to the second plurality of electric contacts.

15. The detector of claim 14, wherein the distribution layer further comprises a plurality of conductive pads, wherein the vias are connected to the conductive pads.

16. The detector of claim 15, wherein the first plurality of electric contacts are bonded to the conductive pads.

17. The detector of claim 1, wherein the detector comprises a plurality of pixels arranged in an array.

18. A system, comprising the detector of claim 1 and, a radiation source or an electron source.

19. A detector comprising:
a radiation absorption layer comprising an electric contact;
a filter electrically connected to the electric contact and configured to attenuate signals from the electric contact below a first cutoff frequency;
an integrator electrically connected to the filter and configured to integrate signals from the filter over a period of time;
wherein the radiation absorption layer comprises a first plurality of electric contacts and is configured to generate electrical signals on the first plurality of electric contacts from radiation incident on the radiation absorption layer;
wherein the detector further comprises an electronics layer comprising a second plurality of electric contacts and an electronic system, wherein the electronic system is electrically connected to the second plurality of electric contacts and is configured to process or interpret the electrical signals;
wherein the detector further comprises a distribution layer configured to electrically connect the first plurality of electric contacts to the second plurality of electric contacts, wherein the radiation absorption layer or the electronics layer comprises the distribution layer;
wherein the first plurality of electric contacts and the second plurality of electric contacts have different spatial distributions.

20. The detector of claim 19, wherein the radiation absorption layer is configured to generate charge carriers from radiation particles incident thereon, and the electric contact is configured to collect a portion of the charge carriers.

21. The detector of claim 19, wherein the radiation absorption layer comprises GaAs.

22. The detector of claim 19, wherein the radiation absorption layer produces a first component of dark noise, wherein the first component of dark noise is below the first cutoff frequency.

23. The detector of claim 19, wherein the detector comprises a plurality of pixels arranged in an array.

24. A system, comprising the detector of claim 19 and, a radiation source or an electron source.

* * * * *